United States Patent [19]

Michalski et al.

[11] Patent Number: 5,777,081

[45] Date of Patent: Jul. 7, 1998

[54] PROCESS FOR PRODUCING AN INTER-ALPHA-TRYPSIN INHIBITOR CONCENTRATE FOR THERAPEUTIC USE AND CONCENTRATE THUS OBTAINED

[75] Inventors: Catherine Michalski, Lille; Jacques Mizon, Lambersart, both of France

[73] Assignee: Association Pour L'Essor de la Transfusion Sanguine Dans la Region Du Nord, Lille, France

[21] Appl. No.: 632,460

[22] PCT Filed: Oct. 17, 1994

[86] PCT No.: PCT/FR94/01197

§ 371 Date: May 17, 1996

§ 102(e) Date: May 17, 1996

[87] PCT Pub. No.: WO95/11260

PCT Pub. Date: Apr. 27, 1995

[30] Foreign Application Priority Data

Oct. 18, 1993 [FR] France ................... 93 12346

[51] Int. Cl.[6] ................... C07K 14/81; A61K 38/17
[52] U.S. Cl. ................... 530/380; 530/395; 530/415
[58] Field of Search ................... 530/380, 395, 530/415

[56] References Cited

U.S. PATENT DOCUMENTS

| | | | |
|---|---|---|---|
| 4,119,774 | 10/1978 | Andersson et al. | 536/21 |
| 4,395,396 | 7/1983 | Eibl et al. | 514/2 |
| 4,629,567 | 12/1986 | Bollen et al. | 210/635 |
| 4,760,130 | 7/1988 | Thompson et al. | 530/350 |
| 5,445,958 | 8/1995 | Feldman | 435/214 |
| 5,457,181 | 10/1995 | Michalski et al. | 530/381 |

OTHER PUBLICATIONS

Salier et al. (1981) *J. Immunol. Meth.*, 47(2), "Inter–α–Trypsin–Inhibitor (ITI): Use of Immunoabsorbents for Preparation of Anti–ITI Antiserum, ITI–Free Human Serum and Purified ITI", pp. 239–248.

Salier et al. (1983) *Anal. Biochem.*, 133(2), "Inter–α–Trypsin–Inhibitor (ITI): Use of New Antisera for Qualitative Studies and Discrete Quantitation of ITI and its Derivatives", pp. 336–343.

Jochum et al. (1983) *Hoppe Seyler's Z. Physiol. Chem.* 364(12), "Inter–α–Trypsin–Inhibitor of Human Serum: An Inhibitor of Polymorphonuclelar Granulocyte Elastase", pp. 1709–1715.

Alberts et al. (1983) "Molecular Biology of the Cell", Garland Publishing, New York, pp. 702–705.

Michalski et al. (1994) *Vox Sang.* 67(4), "Preparation and Properties of a Therapeutic Inter–α–Trypinsin–Inhibitor Concentrate from Human Plasma", pp. 329–336.

*Primary Examiner*—Jon P. Weber
*Attorney, Agent, or Firm*—Birch, Stewart, Kolasch & Birch, LLP

[57] ABSTRACT

A process is disclosed for preparing human inter-alpha-trypsin inhibitor (ITI) from human plasma which comprises two steps of anion exchange chromatography followed by a step of affinity chromatography on immobilized heparin. The process also includes a viral inactivation treatment. The quality of the ITI concentrate obtained is suitable for therapeutic use.

7 Claims, No Drawings

1

PROCESS FOR PRODUCING AN INTER-ALPHA-TRYPSIN INHIBITOR CONCENTRATE FOR THERAPEUTIC USE AND CONCENTRATE THUS OBTAINED

FIELD OF THE INVENTION

The present invention relates to a process for producing an inter-alpha-trypsin inhibitor (ITI) concentrate from a human plasma fraction and the concentrate obtained by said process which is suitable for therapeutic use.

BACKGROUND OF THE INVENTION

ITI is a serine-protease inhibitor found in plasma. Its name derives from its activity as a trypsin inhibitor and from its electrophoretic mobility located between that of $\alpha_1$ and $\alpha_2$ globulins (thus "inter-alpha").

ITI belongs to the "Kunitz-type inhibitors" family (1–4) and consists of 3 polypeptidic chains, two heavy H1 and H2 and one light, called bikunin, the whole being linked by a glycosaminoglycan (GAG) chain. The light chain is responsible for the antiprotease activity. ITI is a glycoprotein with a molecular mass of 220,000 Da.

ITI is synthesized in the liver and circulates in plasma at a concentration of about 0.5 g/l.

ITI is very sensitive to the action of numerous proteases which degrade it into derivatives of lower molecular weight. Among them UTI (urinary trypsin inhibitor derived from bikunin) is finally found in urine which has allowed its isolation and the study of its properties (5,6); this fragment is responsible for many ITI activities and, in particular, its antiprotease activity.

The physiological role of ITI is not yet totally understood. It shows antiprotease activities, in particular as trypsin and chymotrypsin inhibitor, as inhibitor of elastase and cathepsin G which are liberated by the activation of neutrophil polynuclear cells, as plasmin and kallikrein inhibitor. It could also have a growth factor activity for endothelial cells (7).

Moreover a series of studies on UTI indicate that this part of the molecule can play a role in inflammatory-type disorders such as pancreatitis, polyarthritis, septic choc and secondary symptoms associated with treatment of certain cancers (8–10).

ITI could be considered as a pro-inhibitor able to generate active fragments, for example by the action of proteases liberated during inflammatory reactions, said fragments being able to diffuse into the intercellular spaces and to participate to tissue protection against proteases.

It could thus be advantageous to get a preparation of native ITI, for therapeutic use, which could have a longer half-life and an in situ activity closer to the natural activity than that of UTI (11).

Several papers describe attempts to purify native ITI from plasma, either with ammonium sulfate or PEG followed by anion exchange chromatography, or by affinity chromatography with a zinc chelator or on Blue-Sepharose (12–14). Those various processes require the addition of protease inhibitors to avoid rapid degradation of ITI; these inhibitors are usually incompatible with a therapeutic use; moreover the yields are generally very low.

SUMMARY OF THE INVENTION

The Applicant has thus tried to develop a new process for purifying ITI, from human plasma, applicable on an industrial scale and resulting in a molecule with similar biological and structural properties as the native molecule.

The Applicant has taken advantage of a process for producing a high purity concentrate of blood coagulation Factor IX that he has developed (15, 16, and EP 0 317 376) and that provides a fraction which has not been used industrially until now and which is particularly rich in ITI. It is one aim of the present invention to develop a process for purifying ITI from this fraction, without interfering with the yield of recovery of other blood components.

The Applicant has thus revealed an affinity of ITI for sulfate glycosaminoglycans (like heparin) and has taken advantage of this unexpected property to develop a separation process by affinity chromatography on an immobilized sulfate glycosaminoglycan column, for example on a Sepharose® gel, with a mild elution in the presence of 0.2M NaCl.

The Applicant has shown that this process was particularly efficient on a large scale (i.e. with plasma volumes possibly greater than 2,000 liters).

The Applicant has included the affinity chromatography separation of the invention into the plasma protein separation process (as mentioned above). The invention also covers the use of affinity chromatography on sulfate glycosaminoglycan in order to purify ITI starting from any other fraction resulting of a process for separating plasma proteins more particularly developed to optimize the production of another factor.

DETAILED DESCRIPTION OF THE INVENTION

According to one preferred embodiment the process of the present invention comprises the following successive steps:

after plasma cryoprecipitation the supernatant is collected and subjected to anion exchange chromatography on a DEAE (diethylaminoethyl)-gel, more precisely on DEAE-Sephadex® A-50, in sodium citrate buffer at about 0.01M and pH 7;

after discarding fractions containing albumin, γ-globulins, antithrombin III and α-antitrypsin, and washing in the presence of 0.23M NaCl, the addition of 0.5M NaCl to the buffer allows elution of the prothrombin complex concentrate (PCC) which contains ITI together with proteins C and S;

the eluated PCC fraction is subjected to viral inactivation treatment by solvent-detergent (tri(n-butyl)phosphate (TnBP)/Tween), then to an anion exchange chromatography on a DEAE-gel, more precisely on DEAE-Sepharose®, in sodium-phosphate buffer at about 6 mM and pH 6, which eliminates the solvent-detergent in the filtrate; after washing of the column in the presence of 0.23M NaCl, 2 fractions are successively eluted:

the first, after the addition of 5 mm trisodium citrate and 0.28M NaCl contains ITI, the second, after the addition of 0.36M NaCl contains Factor IX;

the ITI containing fraction is subjected to a hromatography on heparin-Sepharose® in sodium-citrate buffer at about 40 mM and pH 7.45, which eliminates proteins C and S in the filtrate and adsorbs the other proteins; elution by adding 0.2M NaCl allows the recovery of a fraction wherein 90% of the proteins are native ITI;

after ultrafiltration and distribution, the ITI samples are further freeze-dryed.

A major advantage of the process according to the invention is the quickness of its implementation (about 10 hours per step) which is particularly important for a very labile molecule like ITI.

The quality of the preparation of ITI concentrate obtained by the process according to the invention was evaluated by electrophoresis and chromatography:

on polyacrylamide gel electrophoresis in the presence or absence of SDS one can see a single major band at a Mr of about 220.000 Da. In the absence of SDS no aggregates and few denaturation products are visible; the visible band corresponds to more than 90% of the proteins;

by high pressure gel filtration one confirms the purity higher than 90% of the native ITI.

The ITI molecule of the concentrate obtained by the process of the invention thus shows a structure similar to that of native ITI which means it is formed of 3 peptidic chains, as demonstrated by polyacrylamide gel electrophoresis after chondroitinase digestion.

The specific activiy of the ITI concentrate was evaluated by its antitrypsin activity (measured according to conventional technique with a chromogenic substrate, LBAPNA) to be 420–500 mU/mg of protein.

The characteristics of the ITI concentrate according to the invention render this preparation especially suitable for a therapeutic use for humans, among others for treating severe inflammatory disorders.

REFERENCES

1 Salier J P: Inter-alpha-trypsin inhibitor: emergence of a family within the Kuitz-type protease inhibitor superfamily. Trends Biochem. Sci. 1990; 15:435–439

2 Balduyck M, Mizon J: l'inter-alpha-trypsine inhibiteur et ses dérivés plasmatiques et urinaires Ann. Biol. Clin. 1991; 49:273–281

3 Steinbuch M: The inter-alpha-trypsin inhibitor. Meth. Enzymol., 1976 45:760–772

4 Gebhard W, Hochstrasser K: Inter-alpha-trypsin inhibitor and its close relatives. In: Barrett, Salvesen, Proteinase inhibitors (Elsevier), 1986; 389–401

5 Balduyck M, Hayem A, Kerckaert J P, Mizon C, Mizon J: Isolation of a human urinary trypsin inhibitor. Biochem. Biophys. Res. Comm., 1982; 109 : 1247–1255

6 Balduyck M, Mizon C, Loutfi H, Richet C, Roussel P, Mizon J: The major urinary trypsin inhibitor is a proteoglycan. Eur. J. Biochem., 1986 158 417–422

7 McKeehan WL, Sakagani Y, Hoschi H, McKeehan K A: Two apparent human endothelial cell growth factors from human hepatoma cells are tumor-associated proteinase inhibitors. J. Biol. Chem., 1986; 261 5378–5383

8 Yagi M, Tomita K, Onoda H, Konishi K, Miyazaki I: Serum granulocyte elastase and superoxyde dismutase activity after administration of protease-inhibitor to postoperative patients. J. Clin. Biochem. Nutr., 1989; 6:221–225

9 Korenaga D, Orita D, Kakeji Y, Haraguchi M, Maehara Y, Sugimachi K. Prophylactic administration of urinary trypsin inhibitor prevents post-operative hyperamylasemia after R2 gastrectomy in patients with gastric cancer—A prospective randomized trial. Bir. Surg. Res. 1989; 23 214–221

10 Matsuo O, Tanaka S, Kikuchi H. Effect of urinary trypsin inhibitor on osteoarthritis. Thromb. Res. 1988; 52:237–245

11 Jönsson-Berling B M, Ohlsson K. Distribution and elimination of intravenouly injected urinary trypsin inhibitor. Scand. J. Clin. Lab. Invest. 1991; 51: 549–557

12 Salier J P, Martin J P, Lambin P, McPhee H., Hochstrasser K. Purification of the human serum inter-alpha-trypsin inhibitor by zinc-chelate and hydrophobic interaction chroratographies. Anal. Biochem. 1980; 109: 273–283

13 Lambin P, Fine J M, Steinbuch M. Nouvelles données sur une antiprotéase du plasma humain: l'inter-alpha-trypsine inhibiteur. Rev. Fr. Transf. Immunohematol. 1975; XVII:385–400

14 Enghild J J, Thogersen I B, Pizzo S V, Salvesen G. Analysis of ITI and a novel trypsin inhibitor, pre-alpha-trypsin inhibitor from human plasma. J. Biol. Chem. 1989; 264:15975–15981

15 Michalski C, Bal F, Burnouf T, Goudemand M. Large scale production and properties of a solvent-detergent treated factor IX concentrate from human plasma. Vox Sang. 1988; 55:202–210

16 Burnouf T, Michalski C, Goudemand M, Huart JJ. Properties of a highly purified human plasma factor IX:c therapeutic concentrate prepared by conventional chromatography. Vox Sang 1989; 57 225–232

The following examples provide an embodiment of the process of the invention and a characterization of the product of the invention, without however limiting its scope.

EXAMPLE I

A batch of plasma intended to preparing a high purity Factor IX concentrate is subjected to the conventional process until PCC is obtained.

In summary, fresh or frozen-thawed plasma is subjected to cryoprecipitation in order to eliminate Factor VIII, factor von Willebrand, fibrinogen and fibronectin. The supernatant (from 1000 to 1500 liters) is harvested and subjected to chromatography on DEAE-Sephadex® gel, (1.5 g per liter of supernatant) in 0.01M sodium citrate at pH 7.0. Albumin, γ-globulins, AT III and $\alpha_1$-antitrypsin are found in the filtrate. The column is washed with the same buffer supplemented with 0.23M NaCl and the PCC fraction is eluted by the addition of 0.5M NaCl in the buffer. This fraction contains up to 20 to 40% by weight of the ITI proteins (which were until now considered as a major contaminant). This fraction is adjusted to 40 g of proteins/l and an osmolarity of 290 mOsm/l at pH 7 and supplemented with 2.5 g/l of lysine.

This fraction is subjected to viral inactivation treatment by contact with TnBP/Tween(final concentration 0.3% tri (n-butyl)phosphate—1% Tween 80) at 24° C for 6 hours.

This fraction is further subjected to chromatography on DEAE-Sepharose® Fast Flow (FF) gel in 6 mM sodium phosphate buffer at pH 6.0. 10 to 12 liters of PCC are injected on a column filled with 18 liters of DEAE-Sepharose®. The mixture of TnBP/Tween is eliminated in the filtrate. The column is washed twice with 5 mM sodium phosphate—5 mM trisodium citrate buffer at pH 6.0, supplemented with 0.16M NaCl followed with 0.23M NaCl. The ITI containing fraction is then eluted by increasing the NaCl concentration to 0.28M. Finally the NaCl concentration is increased to 0.36M to elute the Factor IX enriched fraction which will be further purified by an additional chromatography.

The ITI enriched fraction is adjusted to 40 g proteins/l at 100 mOsmol/l and pH 7.45. It is subjected to chromatography on heparin-Sepharose® in 40 mM trisodium citrate buffer at pH 7.45. Two liters of the concentrate fraction are used for a column of 18 liters of gel. Proteins C and S are eliminated in the filtrate; the other components of the fraction are adsorbed on the column. The column is washed with the same buffer supplemented with 0.05 M NaCl which eliminates Factor X and degraded forms of ITI. The ITI is eluted by adding 0.2M NaCl in the buffer. The eluted fraction contains more than 90% (in weight of proteins) of ITI.

The NaCl concentration may not be higher than 0.2M to avoid aggregate formation.

After concentrating to about 8 g/l ITI is ultrafiltered in 1 g/l citrate—9 g/l NaCL buffer optionally supplemented with 4.5 g/l arginine and 4.5 g/l lysine, at pH 7. The concentrate is adjusted at an osmolarity of about 300 mOsm/l at pH 7, sterile filtered, dispensed in vials and freeze-dried.

EXAMPLE II

Biochemical characteristics of the obtained ITI concentrate

1) The anti-trypsin activity is measured under conventional conditions on L-BAPNA chromogenic substrate (α-N-benzoyl-L-arginin-p-nitroanilide):

the concentrate activity is 3,500–4,500 mU/ml the specific activity is 420–500 mU/mg of protein.

The residual amounts of proteins C and S and Factor X are lower than 0.5 UI/ml. Traces of $C_4$ are detected by Ouchterlony technique and reach less than 0.1 mg/ml (by immunonephelemetry).

2) Electrophoresis on cellulose acetate reveals a single band, which migrates between $\alpha_1$ and $\alpha_2$ globulins.

3) Electrophoresis on polyacrylamide gel, stained with Coomassie Blue, reveals a single major band with Mr 220,000 Da which represents at least 95% of the total proteins of the sample (molecular weight calibration standards were thyroglobulin, Mr 660,000, ferritin, Mr 440,000, catalase, Mr 232,000, aldolase, Mr 150,000 and serumalbumin, Mr 67,000).

4) After ITI digestion by chondroitinase the analysis of polyacrylamide gel electrophoresis in the presence of SDS reveals that the major Mr 220,000 band has completely disappeared and the 2 heavy chains, H1, Mr 96,000 and H2, Mr 86,000, and bikunin (devoid of GAG) Mr 20,000, are visible (molecular weight calibration standards were myosin, Mr 200,000, β-galactosidase, Mr 116,000, phosphorylase B, Mr 97,000, bovine serumalbumin, Mr 67,000 and ovalbumin, Mr 45,000).

5) The homogeneity of the preparation was controlled by size-exclusion chromatography.

EXAMPLE III

Safety of the ITI concentrate in animal models

The freeze-dried concentrate was reconstituted (total amount of proteins: 8 g/l) and controlled in several animal models.

1) Possible toxicity was tested in 10 mice by intraveinous injection of 0.5 ml per 20 g of body weight. After 7 days neither mortality nor lethal effect was observed.

2) Potential thrombogenicity was checked in the rabbit Wessler stasis model after intraveinous infusion at a dose of 10 ml/kg. No blood clot was observed thus confirming the absence of thrombogenic components of the coagulation cascade.

3) The absence of contaminants like vasoactive substances (protein aggregates or peptides released by High Molecular Weight (HMW)-kininogen was controlled in rats, by measuring the heart rythm and blood pressure after intraveinous infusion of 4 ml/kg at 0.1 ml/sec. Both parameters remain constant (±2% variation) after infusion.

4) Absence of pyrogenicity was tested in rabbits according to the European Pharmacopea, at a dose of 2 ml/kg.

We claim:

1. A process for producing an inter-alpha-trypsin inhibitor (ITI) concentrate for therapeutic use, from a human plasma fraction enriched in ITI, comprising a step of affinity chromatography on heparin which has been immobilized on gel, and recovering said ITI concentrate, wherein the ITI in said concentrate consists of three peptidic chains and has a molecular mass of about 220 kDa as determined by SDS polyacrylamide gel electrophoresis.

2. A process according to claim 1, wherein the plasma fraction which is enriched in ITI is obtained after two successive separation steps by chromatography on anion exchange gels.

3. A process according to claim 2, further comprising a viral inactivation treatment with solvent-detergent before the second anion exchange chromatographic step.

4. A process for producing an inter-alpha trypsin inhibitor (ITI) concentrate for therapeutic use, comprising the following sequential steps:

a) subjecting a supernatant of a cryoprecipitated plasma to anion exchange chromatography on a DEAE-grafted gel, in about 0.01 mM sodium citrate buffer at pH 7;

b) eluting a prothrombin complex concentrate (PCC) and ITI containing fraction from the chromatography column of step a) by adding 0.5M NaCl into the buffer;

c) subjecting the fraction which is eluted in b) to viral inactivation treatment with solvent-detergent followed by anion exchange chromatography on a DEAE-grafted gel, in about 6 mM sodium phosphate buffer at pH 6;

d) eluting an ITI containing fraction from the chromatography column of step c) by adding 5 mM trisodium phosphate and 0.28M NaCl into the buffer;

e) subjecting the fraction eluted in d) to chromatography on immobilized heparin in about 40 mM sodium citrate buffer at pH 7.45;

f) eluting a concentrated ITI containing fraction from the chromatography column of step e) by adding 0.2M NaCl into the buffer, wherein ITI represents 90% of the total protein; and g) concentrating the fraction eluted in f) by ultrafiltration, and then dispensing the concentrate into portions and freeze drying the portions, wherein the ITI in said concentrate consists of three peptidic chains and has a molecular mass of about 220 kDa as determined by SDS polyacrylamide gel electrophoresis.

5. A process according to claim 4, wherein the immobilized heparin chromatography of step e) is performed on heparin-Sepharose®.

6. Human inter-alpha-trypsin inhibitor (ITI) concentrate for therapeutic use obtained by a process for producing an (ITI) concentrate for therapeutic use, from a human plasma fraction enriched in ITI, comprising a step of affinity chromatography on heparin which has been immobilized on gel, wherein the ITI in said concentrate has a structure consisting of three peptidic chains and has a molecular mass of about 220 kDa as determined by SDS polyacrylamide gel electrophoresis.

7. Human ITI concentrate according to claim 6, wherein the ITI has a specific activity of 420–500 mU/mg of protein.

* * * * *